United States Patent [19]
Rath et al.

[11] Patent Number: 4,614,590
[45] Date of Patent: Sep. 30, 1986

[54] DIALYSIS APPARATUS AND METHOD FOR ITS CONTROL

[75] Inventors: Dieter Rath; Peter Seeck, both of Melsungen, Fed. Rep. of Germany

[73] Assignee: Intermedicat GmbH, Emmenbrucke, Switzerland

[21] Appl. No.: 655,731

[22] Filed: Sep. 28, 1984

[30] Foreign Application Priority Data

Oct. 1, 1983 [DE] Fed. Rep. of Germany ....... 3335744

[51] Int. Cl.$^4$ ............................................. B01D 13/00
[52] U.S. Cl. .................................... 210/637; 210/646; 210/90; 210/321.3; 604/5
[58] Field of Search .................... 210/90, 637, 321.3, 210/137, 646; 604/4, 5, 6

[56] References Cited

U.S. PATENT DOCUMENTS

4,490,134 12/1984 Troutner .................................. 604/5
4,514,295 4/1985 Mathieu et al. ....................... 210/90

*Primary Examiner*—Frank Spear
*Attorney, Agent, or Firm*—Kenyon and Kenyon

[57] ABSTRACT

A dialysis apparatus utilizes an expansion chamber in parallel with a pump from which the chamber receives blood via a valve. During the return flow phase the pump rotates in the same direction; but, the valve is closed and a valve at the chamber outlet is opened. The pump draws blood from the chamber and transports it to a dialyzer. A control device regulates the pump and valves depending on the time integral of the pump delivery. In each phase, blood is transported until the chamber has received or discharged a predetermined volume. The pump speed is variable during operation.

11 Claims, 2 Drawing Figures

DIALYSIS APPARATUS AND METHOD FOR ITS CONTROL

BACKGROUND OF THE INVENTION

1. Field of the Invention

The present invention relates generally to medical apparatus and methods, and more specifically to such apparatus and methods for dialyzing blood.

2. Description of the Prior Art

Various dialysis devices for single-needle dialysis are known. In single-needle dialysis, a single one-lumen cannula is inserted into a blood vessel of the patient. Connected to the cannula is a blood line, which branches into an arterial line and a venous line. A blood pump conveys the blood from the patient via the arterial line into an expansion chamber. In a second phase, the arterial line is closed off and the venous line opened. Now the blood is pumped out of the expansion chamber to a dialyzer and is thence returned to the patient via the open venous line. As a rule, two pumps are employed, one of which draws blood from the arterial line and the other which pumps blood into the venous line. Hose pumps are used, the delivery of which is proportional to the pump speed.

In a known dialysis apparatus of the above mentioned kind, the expansion chamber for the temporary uptake of the blood drawn through the arterial line is arranged between the arterial line and the pump. The pump outlet leads to the dialyzer. The dialyzer outlet is coupled to the venous line via a bubble trap. The arterial line and the venous line each contain a shutoff valve, both shutoff valves being pinched hose valves, and being operated alternately, so that one line is closed while the other is open. During the inflow phase the shutoff valve of the arterial line is open. The pump then draws blood through the arterial line into the expansion chamber, from which a corresponding volume of air is displaced. After the pressure in the venous line has risen to a certain value, the shutoff valve in the arterial line is closed and the shutoff valve in the venous line is opened. The blood present in the expansion chamber is pumped out by the blood pump which continues to run, and is supplied to the venous line via the dialyzer and the bubble trap. The switching between the inflow phase and the return flow phase depends on pressure measurements made at two different points of the closed blood circulation system.

The dialysis apparatus of the prior art entails certain disadvantages. The determination of pressure requires pressure lines and pressure measuring devices which are expensive, and susceptible to alteration with time that adversely affects the accuracy of the switching timing. Further the limit values of the pressure switching may be incorrectly adjusted. Another disadvantage resides in the fact that the permanently running pump always pumps into the venous line. When the venous line is shut off, the pressure in it increases to the limit value. When the limit value is reached, the shutoff valve in the venous line opens and the pressure discharges via the cannula into the blood vessel. But, at the same time, the pump continues to run, so that the normal pump delivery superimposes itself on the pressure discharge. This results in strong fluctuations in the quantity of blood supplied to the patient.

SUMMARY OF THE INVENTION

An object of the present invention is to provide a dialysis apparatus of the above variety which draws blood from a patient in the inflow phase at a constant flow rate, and returns the blood to the patient in the return flow phase also at a constant flow rate, that is, without pressure discharge. To achieve this result, the expansion chamber of the present invention is disposed in a closable, parallel circuit with the pump.

In accordance with the present invention, the quantity of blood drawn from the patient is determined in the inflow phase exclusively by the delivery rate of the pump. The pump pumps from the arterial line into the expansion chamber. No pressure can develop in the direction of the venous line. During the return flow phase, the pump conveys the blood from the expansion chamber into the venous line via the dialyzer. The pressure that has built up in the expansion chamber can then not discharge abruptly, as the reduction of this pressure occurs via the blood pump.

The dialysis apparatus according to the invention operates with a single one lumen cannula and with a single pump. This pump is used for the metered filling of the expansion chamber as well as for the metered evacuation of the expansion chamber. During the inflow phase the blood passes via the pump into the expansion chamber, and during the return flow phase the blood leaves the expansion chamber again via the pump, in order to be supplied to the dialyzer. The quantity of blood taken from the arterial line depends exclusively on the pump speed, and the quantity of blood which is pumped into the venous line also depends exclusively on the pump speed. In this way the patient's blood system is not exposed to any great temporary pressure fluctuations.

Preferably, the parallel circuit before the expansion chamber contains a fourth shutoff valve and after the expansion chamber a fifth shutoff valve, which are closed alternately, the fourth shutoff valve being controlled synchronously with the first shutoff valve in the arterial line.

The invention further entails a method for the control of a single-needle dialysis apparatus, where several shutoff valves can be switched between an inflow phase, in which blood from a single one-lumen cannula is conveyed by a pump into an expansion chamber, and a return flow phase, in which blood is conveyed from the expansion chamber to the cannula via the pump and a dialyzer.

According to the method of the present invention, during the inflow phase, the time integral of the pump delivery is formed and compared with the capacity of the expansion chamber. In case of equivalence, the shutoff valves are switched to the return flow phase. During the return flow phase, the time integral of the pump delivery is formed, compared with the chamber capacity, and in case of equivalence, the values are again switched to the inflow phase.

The method of the present invention permits very accurate control of the timing of the inflow and return flow phases, without the need for carrying out pressure measurements for the control cycle. The delivery rate of the pump can be either manually altered, or programmed to assume different values between the inflow and return flow phases. Since the delivery of the pump is proportional to the pump speed, the time which the pump takes to fill the expansion chamber with blood, or to evacuate it can easily be calculated. The delivery rate of the pump can be changed during each phase. In any event, it is assured that the expansion chamber is completely filled during the inflow phase, and pumped out during the return flow phase. Pressure measurements may be provided at various points of the system to monitor the operation; but, they are not necessary for the control of the shutoff valves and the pump.

DESCRIPTION OF THE PREFERRED EMBODIMENTS

Figure 1:
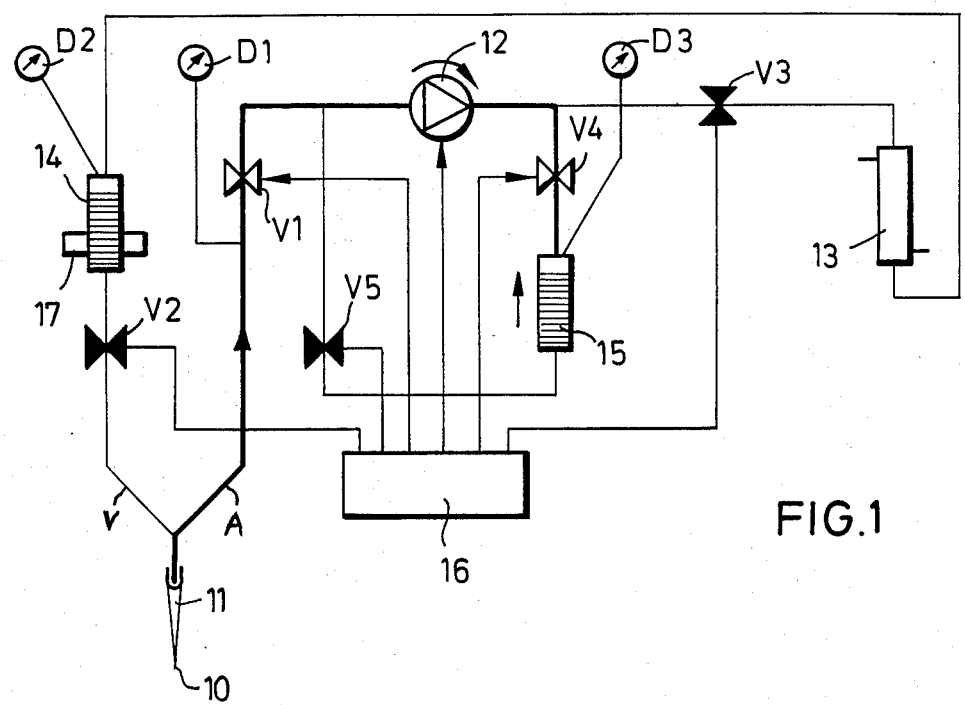
FIG. 1 is a schematic diagram of a preferred embodiment of the invention during an inflow phase.

The present invention entails a dialyzing apparatus and method. Referring to FIG. 1, a one-lumen needle cannula 10, the tip of which is inserted into a blood vessel of the patient, is coupled to a blood line 11. The blood line 11 branches into an arterial line A and a venous line V. In the arterial line A a first shutoff valve V1 is provided, and in the venous line V, a second shutoff valve V2. All shutoff valves mentioned here are preferably hose valves which pinch the respective hose line externally and stop the flow through this hose line. The shutoff valves can be remotely controlled by a control device 16, for example via electromagnets.

After the shutoff valve V1, the arterial line A is coupled to the inlet of a pump 12, which is, for example, a hose pump with variable speed of rotation. The pump 12 outlet is coupled via a third shutoff valve V3 to the inlet of a dialyzer 13, and the outlet of the dialyzer 13 is coupled to a bubble trap 14, the outlet of which is coupled to the venous line V containing the second shutoff valve V2.

An expansion chamber 15 is in parallel with the pump 12. The inlet is coupled via a fourth shutoff valve V4 to the pump 12 outlet, and the outlet of the expansion chamber 15 is coupled via a fifth shutoff valve V5 to the pump 12 inlet.

The entire system described until now, including the circuit parallel to the pump 12, is closed. This means that external air cannot enter, and that blood cannot leave the system. The expansion chamber 15 and the bubble trap 14 are tightly closed vessels.

The shutoff valves V1 to V5 and the pump 12 are controlled by the electronic control device 16 in a manner still to be explained.

The dialysis apparatus contains, in addition, some pressure measuring devices for monitoring the system and possibly triggering alarms. A first pressure measuring device D1 is coupled to the arterial line A, to measure the arterial pressure. A second pressure measuring device D2 measures the pressure in the upper region of the bubble trap 14, that is, the venous return flow pressure, and a third pressure measuring device D3 measures the pressure in the upper region of the expansion chamber 15. At the bubble trap 14 there is an air detector 17, which detects, e.g. by acoustic means, the presence of air bubbles in the blood present in the bubble trap 14. The pressure measuring devices D1 to D3 and the air detector 17 may also be coupled to the control device 16, in order to set off an alarm in case of an incorrect operational state and/or to initiate the necessary remedial measures.

Figure 2:
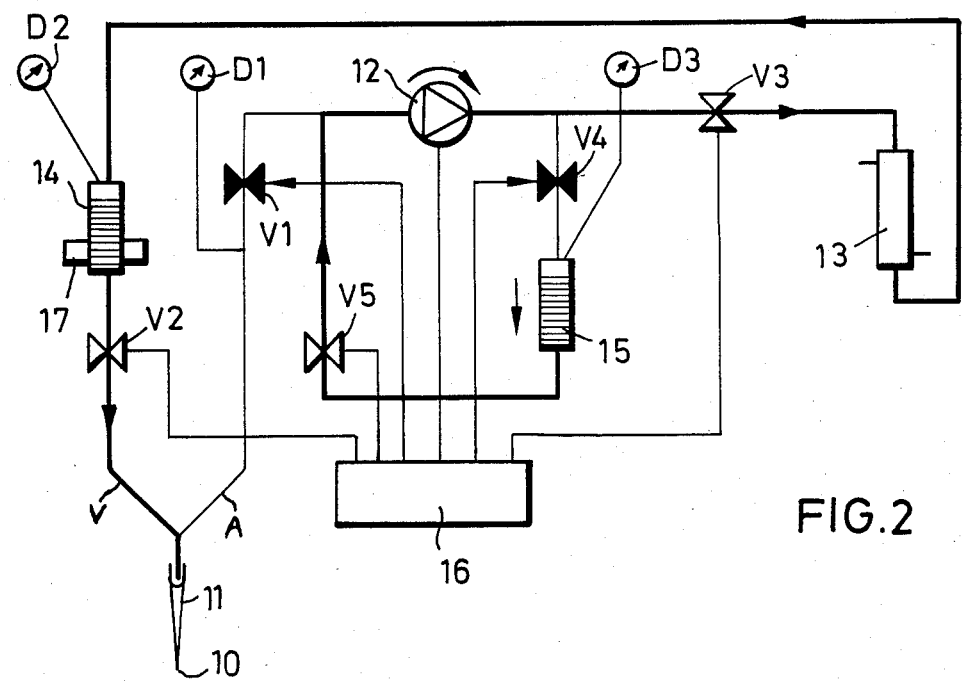
FIG. 2 is a schematic diagram of a preferred embodiment of the invention during a return flow phase.

In FIGS. 1 and 2, open valves are shown white and closed valves black. Referring to FIG. 1, during the blood inflow phase, the blood pump 12 runs at first at the maximum speed. It conveys blood via the open valves V1 and V4 into the expansion chamber 15. In this phase, the valves V2, V3 and V5 are closed.

Referring to FIG. 2, after the pump 12 has delivered a quantity of blood which corresponds to the capacity of the expansion chamber 15, the control device 16 closes the valves V1 and V4 and opens the valves V2, V3 and V5. The blood pump 12 continues to run at the same speed as in the inflow phase, or at an elevated speed. As a rule, the speed of the pump 12 can be increased to the extent that the patient is still without pain from the back-flowing blood. The blood is now cycled back from the expansion chamber 15 through the open valve V5, the pump 12, the open valve V3, the dialyzer 13, the bubble trap 14 and the valve V2, to the patient. This phase lasts until the entire delivered volume in the return flow phase corresponds to the blood volume in the expansion chamber 15, or until a bottom level in the expansion chamber 15 has been reached. At the end of this period the next blood inflow phase is started.

Thus, the switching of the individual cycles is a function of the pump 12 speed. Any pressure measurements that are carried out serve only for checking.

When the dialysis apparatus starts up, first, the blood pump 12 runs, with the valve positions according to the inflow phase in FIG. 1 until the expansion chamber 15 is filled. During this phase, the integral over time of the delivery of the pump 12 is formed and compared with a value corresponding to the capacity of the expansion chamber 15. When the two values have become equal, the control device 16 switches the valve positions to the return flow phase in FIG. 2. The pump 12 then draws blood out of the expansion chamber 15 in order to send this blood to the dialyzer 13 through the opened valve V3. Again the integral over time of the particular delivery output of the pump 12 is formed. That is, the quantity of blood transported since the beginning of the return flow phase is measured and compared with the preselectable capacity of the expansion chamber 15. When bottom level status has been reached, the next cycle is executed.

The pump speed can be adjusted during operation of the dialysis apparatus. In that case, the time for the inflow phase or, respectively, for the return flow phase changes automatically.

It is possible that during the dialysis the given pressure limits are exceeded due to faulty operation or external intervention. For safety reasons, immediate switching to the next cycle takes place in such a case. An optical and acoustic alarm is set off only if the pressure limits are again surpassed in a fixed period of time, and the system is then switched to the safe position.

While the invention has been described in its preferred embodiments, it is to be understood that the words which have been used are words of description rather than limitation and that changes may be made within the purview of the appended claims without departing from the true scope and spirit of the invention in its broader aspects.

We claim:
1. An apparatus for dialyzing blood, comprising:
   means for puncturing a blood vessel;
   a blood line, coupled to said puncturing means, branching into an arterial line and a venous line;

means, coupled to said arterial line, having an inlet and an outlet, for pumping blood through said blood line;

said blood line comprising a circuit disposed in parallel with said pumping means;

first valve means, coupled to said arterial line between said pumping means and said puncturing means, for opening and closing said arterial line;

second valve means, coupled to said venous line, for opening and closing said venous line;

means, coupled to said blood line between said pumping means and said venous line, for dialyzing blood in said blood line; and, means, coupled to said circuit, for temporarily accumulating blood in said blood line.

2. An apparatus as in claim 1 further comprising third valve means, coupled to said blood line between said outlet of said pumping means and said dialyzing means, for opening and closing said blood line.

3. An apparatus as in claim 2 further comprising:

fourth valve means, coupled to said circuit between said outlet of said pumping means and said blood accumulating means, for opening and closing said circuit; and, fifth valve means, coupled to said circuit between said inlet of said pumping means and said blood accumulating means, for opening and closing said circuit.

4. An apparatus as in claim 3 further comprising means, coupled to said pumping means and to said first, second, third, fourth and fifth valve means, for controlling said first, second, third, fourth and fifth valve means.

5. An apparatus as in claim 4 wherein said controlling means comprises:

evaluating means, coupled to said pumping means, for forming, during an inflow phase, a first time integral of a delivery of said pumping means and for comparing said first time integral with a predetermined capacity of said accumulating means; for forming, during a return flow phase, a second time integral of said delivery of said pumping means and for comparing said second time integral with said predetermined capacity of said accumulating means; and, switching means, coupled to said evaluating means and said first, second, third, fourth and fifth valve means, for, when said first time integral substantially equals said capacity, opening said second, third and fifth valve means and closing said first and fourth valve means; and, for, when said second time integral substantially equals said capacity, opening said first and fourth valve means and closing said second, third and fifth valve means.

6. An apparatus as in claim 3 further comprising first pressure means, coupled to said blood line between said dialyzing means and said second valve means, for measuring pressure in said venous line.

7. An apparatus as in claim 6 further comprising second pressure means, coupled to said blood line between said first valve means and said puncturing means, for measuring pressure in said arterial line.

8. An apparatus as in claim 7 further comprising means, coupled to said pumping means and to said first, second, third, fourth and fifth valve means, for controlling said first, second, third, fourth and fifth valve means.

9. An apparatus as in claim 8 wherein said controlling means comprises:

evaluating means, coupled to said pumping means, for forming, during an inflow phase, a first time integral of a delivery of said pumping means and for comparing said first time integral with a predetermined capacity of said accumulating means; for forming, during a return flow phase, a second time integral of said delivery of said pumping means and for comparing said second time integral with said predetermined capacity of said accumulating means; and, switching means, coupled to said evaluating means and said first, second, third, fourth and fifth valve means, for, when said first time integral substantially equals said capacity, opening said second, third and fifth valve means and closing said first and fourth valve means; and, for, when said second time integral substantially equals said capacity, opening said first and fourth valve means and closing said second, third and fifth valve means.

10. An apparatus as in claim 9 further comprising means, coupled to said first and second pressure means, for signaling an improper operational state.

11. A method for controlling a dialysis apparatus having a cannula; a blood line, coupled to said cannula, branching into an arterial line and a venous line; a pump, having an inlet and an outlet, coupled to said arterial line, said blood line including a circuit disposed in parallel with said pump; a first valve, coupled to said arterial line between said pump and said cannula; a second valve, coupled to said venous line; a dialyzer, coupled to said blood line between said pump and said venous line; an expansion chamber, coupled to said circuit; a third valve, coupled to said blood line between said outlet of said pump and said dialyzer; a fourth valve, coupled to said circuit between said outlet of said pump and said expansion chamber; and, a fifth valve, coupled to said circuit between said inlet of said pump and said expansion chamber, said method comprising:

calculating, during an inflow phase, a first time integral of a delivery of said pump;

comparing said first time integral with a predetermined capacity of said expansion chamber;

closing, when said first time integral substantially equals said capacity, said first and fourth valves;

opening, when said first time integral substantially equals said capacity, said second, third and fifth valves;

calculating, during a return flow phase, a second time integral of a delivery of said pump;

comparing said second time integral with said capacity of said expansion chamber;

closing, when said second time integral substantially equals said capacity, said second, third and fifth valves; and, opening, when said second time integral substantially equals said capacity, said first and said fourth valves.

* * * * *